United States Patent [19]

Strekowski et al.

[11] Patent Number: 5,304,554
[45] Date of Patent: Apr. 19, 1994

[54] 4-[(ALKYL OR DIALKYL)AMINO]QUINOLINES AND THEIR METHOD OF PREPARATION

[75] Inventors: Lucjan Strekowski, Stone Mountain; Roman L. Wydra, Atlanta; Steven E. Patterson, Norcross; Raymond F. Schinazi, Decatur, all of Ga.

[73] Assignees: Emory University; Georgia State University Research Foundation, Atlanta, Ga.

[21] Appl. No.: 849,790

[22] Filed: Mar. 11, 1992

Related U.S. Application Data

[63] Continuation of Ser. No. 515,869, Apr. 27, 1990, abandoned.

[51] Int. Cl.$^5$ .................. A61K 31/54; A61K 31/535; A61K 31/495; A61K 31/50
[52] U.S. Cl. .................. 514/228.2; 514/232.8; 514/235.2; 514/254; 514/285; 514/307; 514/313; 544/60; 544/62; 544/125; 544/128; 544/361; 544/363; 546/62; 546/70; 546/144
[58] Field of Search .................. 544/60, 62, 125, 128, 544/361, 363; 546/61, 62, 144, 159, 163, 70; 514/228.2, 232.8, 235.2, 255, 284, 285, 307, 313, 254

[56] References Cited

U.S. PATENT DOCUMENTS

| | | | |
|---|---|---|---|
| 2,785,165 | 3/1957 | Schock et al. | 546/159 |
| 2,981,731 | 4/1961 | Moore et al. | 546/61 |
| 3,755,332 | 8/1973 | Wasley et al. | 260/288 |
| 4,008,278 | 2/1977 | Boudakin et al. | 564/412 |
| 4,560,692 | 12/1985 | Field et al. | 514/313 |
| 4,608,383 | 8/1986 | Wiedemann et al. | 514/407 |
| 4,686,228 | 4/1987 | Campbell et al. | 546/144 |
| 4,959,363 | 9/1990 | Wentland | 514/235.2 |

FOREIGN PATENT DOCUMENTS

| | | |
|---|---|---|
| 206951 | 5/1986 | European Pat. Off. |
| 2551027 | 5/1976 | Fed. Rep. of Germany |
| 2815340 | 12/1978 | Fed. Rep. of Germany |
| 2728073 | 1/1979 | Fed. Rep. of Germany |
| 788130 | 12/1957 | United Kingdom |

OTHER PUBLICATIONS

Chem Abstract vol. 74: 138975f., abstract of Bass et al. (5) (1971).
Bass et al., Journal of Medicinal Chemistry, (1971) 14(4) 275–283.
Singh et al., Journal of Medicinal Chemistry (1971) 14(4) 283–286.
Chem. Abstr. 91:107,574 Trakhtenberg, et al. {including copies of on-line printout!} (1979).
Chem. Abstr. 86:170,620, Gershuns et al. (1977).
Chem. Abstr. 86:25,373 Gershuns et al. (1977).
Chem. Abstr. 83:178,770 Gershuns et al. (1975).
Hahn, et al., *Mil Med.* 131, 1071 (1966).
Denny, et al., *Anti-Cancer Drug Des.* 2, 263 (1987).
Bielavsky, *Coll. Czech. Chem. Commun.* 42, 2802 (1977).
Strekowski, et al., *Heterocycles* 29, 539 (1989).
Strekowski, et al., *Tetrahedron Lett.* 30, 5197 (1989).
Moore, et al., *Tetrahedron Lett.* 20, 1277 (1963).
John, *Ber.* 59, 1447 (1926).
Smalley, "Quinolines," Part I, p. 319, (G. Jones ed., Wiley, London, 1977).
Fuson, et al., *J. Am. Chem. Soc* 68, 1270 (1946).
Knorr, et al., *Ber.* 30, 937 (1897).
John, *J. Prakt. Chem.* 266, 303 (1928).
Wakselman, et al., *J. Chem. Soc., Chem. Commun.* 1701 (1987).

(List continued on next page.)

*Primary Examiner*—Mukund J. Shah
*Assistant Examiner*—Matthew V. Grumbling
*Attorney, Agent, or Firm*—Kilpatrick & Cody

[57] ABSTRACT

Novel 4-[(alkyl or dialkyl)amino]quinolines are disclosed that are prepared by condensing 2-(trifluoromethyl)aniline or its derivative with an alkyl vinyl ketone, and alkyl ketone, an alkyl heteroaryl ketone or a cyclic ketone, to provide the corresponding ketimine, that is anionically cyclized to the quinoline. The quinolines are useful as intercalators of DNA, and also inhibit the replication of retroviruses, including HIV.

9 Claims, 1 Drawing Sheet

OTHER PUBLICATIONS

Ohta, et al., *Heterocycles,* 23(7), 1759 (1985).
Sakamoto, et al., *Synthesis,* 245 (1984).
McNamara, et al., *Tetrahedron,* 40(22), 4685 (1984).
Leardini, et al., *J. Chem. Soc., Chem. Commun.* 1390 (1985).
Miura, et al., *J. Chem., Soc.* PT1, 1021 (1987).
Conjat, et al., *Tetrahedron Letters* 2885 (1975).
Epsztajn, et al., *J. Chem. Soc.,* PT1, 213 (1985).
Walsh, et al., *Tetrahedron Letters* 27(10), 1127 (1986).
Strekowski, et al., *J. Med. Chem.* 29, 1311 (1986).
Strekowski, et al., *J. Med. Chem.* 31, 1231 (1988).
Strekowski, et al., *Anti-Cancer Drug Design* 2, 387, (1988).
Field, et al., Chem Abstract, (1989), 110:75,334k.
DeMarini, et al., *Mutat. Res.* 136(3), 185–99 (1984).
Rastogi, et al., *Indian J. Pharmac.* 19(1), 44–48 (1987).
Prasad, et al., *Indian J. Chem.* 25B, 729–734 (1986).
Shaw, et al., *Nature* 169, 712–713 (1952).
Gershon, *Nature* 186, 1072–1073 (1960).
Bindra, et al., *Indian J. Chem.* 26B, 318–329 (1987).
Asthana, et al., *Indian J. Chem.* 26B, 330–334 (1987).
Yamato, et al., *J. Med. Chem.* 32(6), 1295–1300 (1989).
Finlander, et al., *Heterocycles* 23(6), 1437–1444 (1985).
Matsumoto, et al., *Heterocycles* 22(10), 2313–2316 (1984).
Thummel, et al., *J. Org. Chem.* 49, 2208–2212 (1984).
Jones, et al., *J. Chem. Soc.* (C) 1969, 707–710 (1969).
Boogaerts, et al., *Infection* 14 (Suppl. 2) 258–262 (1986).

n = 1,2
X = -CH=CH-, S,O, -N=CH-, -CH=N-

$R^1$ = H, Cl, OMe, SMe
$R^2$ = any alkylamino, cycloalkylamino, acyclic dialkylamino or cyclic amino with the nitrogen atom as part of the ring. All these substituents $R^2$ may additionally be substituted at the alkyl portions.
$R^4$ = H, alkyl

4-[(ALKYL OR DIALKYL)AMINO]QUINOLINES AND THEIR METHOD OF PREPARATION

BACKGROUND OF THE INVENTION

The United States government has rights in this invention as a result of a grant from the NIAID of the National Institute of Health, Bethesda, Md.

This is a continuation of copending application Ser. No. 07/515,869 filed on Apr. 27, 1990 now abandoned.

The present invention is in the general area of organic chemistry, and specifically relates to new 4-[(alkyl or dialkyl)amino]quinoline derivatives which bind nucleic acid and their method of preparation.

A number of quinolines are used pharmaceutically as antimalarial, antiamoebic, and anesthetic drugs. The structures and numbering schemes for quinoline, (compound 1a) and its related compound, acridine (compound 1b) are provided below.

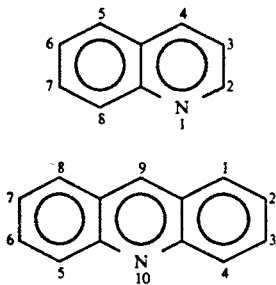

Several aminoquinolines are known that interact with DNA. For example, Hahn, et al., have discovered that chloroquine (7-chloro-4-(4-diethylamino-1-methylbutylamino)quinoline)) and quinacrine (6-chloro-9-[[4-(diethylamino)-1-methylbutyl]amino]-2-methoxyacridine) have antimalarial and antiamoebic activity. F.E. Hahn et al. in *Mil. Med.* 131, 1071 (1966) determined that chloroquine inhibits nucleic acid biosynthesis by forming a molecular complex with DNA. Unfortunately, infants and children are extremely susceptible to adverse effects from high dosages of chloroquine. Sudden deaths have been reported on administration of the compound.

W. A. Denny, et al., in *Anti-Cancer Druo Des.* 2, 263 (1987) investigated the ability of certain quinolines to bind to DNA in a minimal fashion that would be suitable for the treatment of solid tumors remotely located from the site of administration of the drug. They found that 2-phenylquinolines are not active in vivo, and that 2-styrylquinolines bind to DNA too tightly to be used in the treatment of the remote solid tumors.

Cancer is now the second leading cause of death in the United States, Europe, and Japan, resulting in approximately 1,000,000 deaths annually in these countries. In the United States alone, each year over one million people are diagnosed with cancer, and over 500,000 people die from the disease. The number of newly diagnosed cancerous growths in patients in the United States is growing at a rate of 3% a year.

Chemotherapy now represents less than 4% of the total expenditures on the treatment of cancer. Chemotherapy involves the disruption of cell replication or cell metabolism. There are four major classes of chemotherapeutic agents currently in use for the treatment of cancer; anthracyclines, alkylating agents, antiproliferatives, and hormonal agents.

Viral diseases (including acquired immonodeficiency syndrome, or AIDS, caused by human immunodeficiency virus), as well as cancer, involve an undesirable proliferation of nucleic acids within a dysfunctional cell. AIDS was recognized as early as 1979. AIDS is generally accepted at this time to be a consequence of infection with the retrovirus, human immunodeficiency virus (HIV-1). Antibodies to these viruses are present in over 80% of patients diagnosed as having AIDS or pre-AIDS syndrome, and have been found with high frequency in identified risk groups.

A patient is generally diagnosed as having AIDS when a previously healthy person with an intact immune system acquires impaired T-cell immunity. The impaired immunity usually appears over a period of eighteen months to three years following infection. As a result of this impaired immunity, the patient becomes susceptible to opportunistic infections, various types of cancer such as Kaposi's sarcoma, and other disorders associated with reduced functioning of the immune system.

A number of compounds have been found to inhibit HIV activity or replication, including HPA-23, interferons, ribavirin, phosphonoformate, ansamycin, suramin, imuthiol, penicillamine, rifabutin, AL-721, 3'-azido-3'-deoxythymidine (AZT), and other 2',3'-dideoxynucleosides, such as 2',3'-dideoxycytidine (DDC), 2',3'-dideoxyadenosine (DDA), 3'-azido-2',3'-dideoxyuridine (AzddU), 2',3'-didehydrocytidine, 3'-deoxy-2',3'-didehydrothymidine and 3'-azido-5-ethyl-2',3'-dideoxyuridine (AzddEU).

It would be of great pharmaceutical benefit to provide new quinoline derivatives that effectively bind to DNA or RNA in a way that effectively reduces or inhibits unwanted nucleic acid replication, either alone or in combination with another pharmaceutical compound.

Several synthetic routes to quinoline derivatives containing an unsubstituted $NH_2$ group at position 4 are known. J. Bielavsky, *Coll. Czech. Chem. Commun.* 42, 2802 (1977); L. Strekowski et al., *Heterocycles* 29, 539 (1989); L. Strekowski et al., *Tetrahedron Lett.* 30, 5197 (1989); J.A. Moore and L.D. Kornreich, *Tetrahedron Lett.* 20, 1277 (1963); H. John, *Ber.* 59, 1447 (1926). However, these methods are not suitable for the preparation of quinolines with alkylamino (RNH) or dialkylamino ($R_2N$) groups at position 4 of the quinoline.

The 4-alkylamino and 4-dialkylaminoquinolines have traditionally been synthesized by amination of 4-halogenoquinolines that have been prepared from 4-hydroxyquinolines. For a review of this method, see: R.K. Smalley, in "Quinolines," Part I, G. Jones, ed., Wiley, London, 1977, p. 319). As an example, 4-hydroxy-2-phenylquinoline, obtained in the condensation reaction between ethyl anthranilate and acetophenone diethyl ketal (R.C. Fuson and D.M. Burness, *J. Am. Chem. Soc.* 68, 1270 (1946)) Was treated with a mixture of $PCl_5$ and $POCl_3$ to give 4-chloro-2-phenylquinoline (L. Knorr and E. Fertig, *Ber.* 30, 937 (1897)). The latter compound was also prepared from 4-amino-2-phenylquinoline (H. John, *J. Prakt. Chem.* 226, 303 (1928)). Treatment of the chloroquinoline with diisoamylamine at high temperature gave 4-diisoamylamino-2-phenylquinoline in a low yield (H. John, *J. Prakt. Chem.* 226, 303 (1928)). U.S. Pat. No. 4,560,692 describes a similar reaction scheme that can be used to prepare several derivatives of 2-(4-X-phenyl)-4-piperidinoquinolines, where X=H, halogen, or alkyl.

This method of synthesis of 4-alkylamino and 4-dialkylaminoquinolines is difficult because it involves a number of steps and requires the use a toxic reagent ($PCl_5$ or $POCl_3$). It would be much more preferable to have a method of synthesis of these compounds that is more efficient and that utilizes less noxious reagents.

It is therefore an object of the present invention to provide an efficient and convenient process for the preparation of 4-[(alkyl or dialkyl)amino]quinolines.

It is another object of the present invention to provide new quinoline derivatives that can reduce or inhibit replication of nucleic acids.

It is another object of the present invention to provide new quinoline derivatives that can amplify the activity of known anticancer drugs.

SUMMARY OF THE INVENTION

The present invention is a method of synthesis of 4-[(alkyl and dialkyl)amino]quinolines of the formulas:

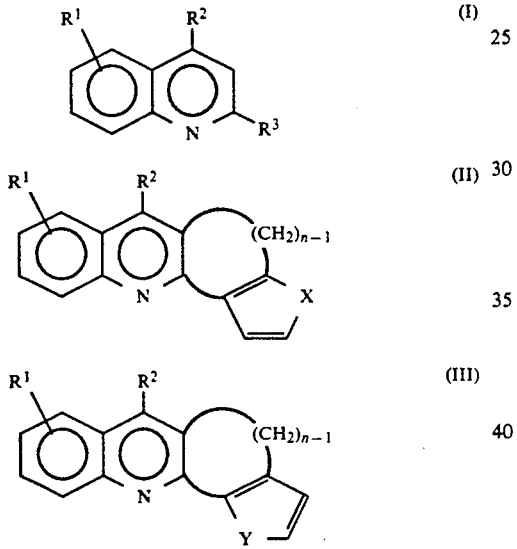

wherein: $R^1$ is H, 2-chloro, 3-chloro, 4-chloro, 5-chloro, 3-methoxy, 4-methoxy, 5-methoxy, or 4-methylthio (numbering scheme based on parent aniline, wherein $NH_2$ is number 1 in the ring); $R^2$ is an alkylamino or dialkylamino group optionally substituted with aprotic substituents; $R^3$ is an alkenyl, aromatic, or heteroaromatic group optionally substituted with aprotic groups; n is 2 or 3; and X and Y are S, O, HC=CH, N=CH, or CH=N.

The new synthetic route to the derivatized quinolines described herein is a significant improvement over the prior art method of preparing 4-[(alkyl or dialkyl)amino]quinolines, because it includes fewer steps and is more efficient and cost effective.

The method includes condensing a 2-(trifluoromethyl)aniline or its derivative with an alkyl vinyl ketone, an alkyl aryl ketone, an alkyl heteroaryl ketone, or a cyclic ketone, to give the corresponding ketimine. The intermediate ketimines have not previously been described in the literature.

The ketimine is then anionically cyclized in the presence of a lithium alkylamide or a lithium dialkylamide to form a derivatized 4-[(alkyl or dialkyl)amino]quinoline. All of the fluorine atoms in the trifuoromethyl group of the ketimine are eliminated during the cyclization.

When prepared from an alkyl vinyl ketone, an alkyl aryl ketone, or an alkyl heteroaryl ketone, the resulting quinoline (structure I) contains an alkenyl, aromatic, or heteroaromatic substituent at position 2 of the quinoline and an alkylamino or dialkylamino (depending on the lithium reagent used) at position 4 of the quinoline. When prepared from a cyclic ketone, a dihydroacridine derivative or a H-indenoquinoline is formed (structures II and III) that has an aromatic ring fused to the saturated ring of the acridine or the H-indenoquinoline, and an alkylamino or dialkylamino group (depending on the lithium reagent used) at position 4 of the quinoline.

A number of the substituted quinolines of structure I prepared according to the method of synthesis described here have not previously been reported, including those wherein $R_3$ is 2,2-dialkylvinyl, biphenyl-4-yl, 2-naphthyl, 2-pyridinyl, 3-pyridinyl, 4-pyridinyl, 2-furanyl, or 2-thienyl optionally substituted with aprotic groups. In addition, dihydrocridines and Hindenoquinolines of structures II and III are likewise new. These new compounds are useful as intercalators of DNA and are capable of amplifying the effect of phleomycin and bleomycin, two anticancer agents. These compounds also exhibit selective in vitro inhibition of retroviruses, including HIV-1, the etiological agent of acquired immunodeficiency syndrome (AIDS).

DETAILED DESCRIPTION OF THE INVENTION

Figure 1:
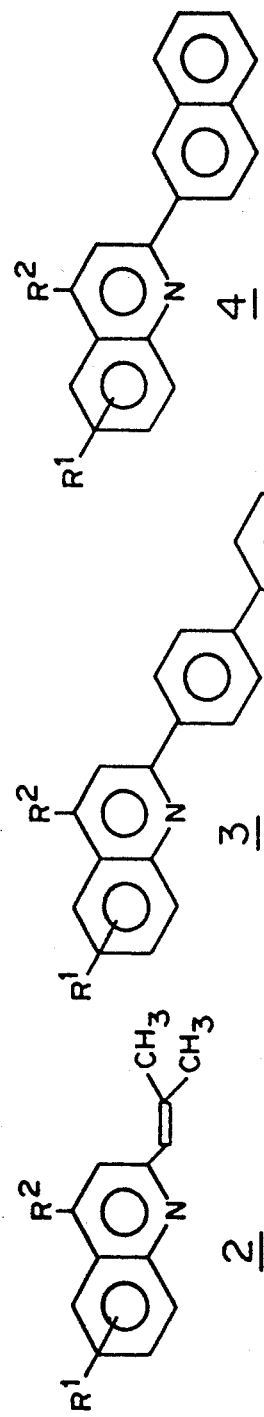
FIG. 1 is an illustration of examples of new 4-[(alkyl or dialkylamino)]quinolines that can be prepared according to the method of synthesis of the present invention.
Figure 1:
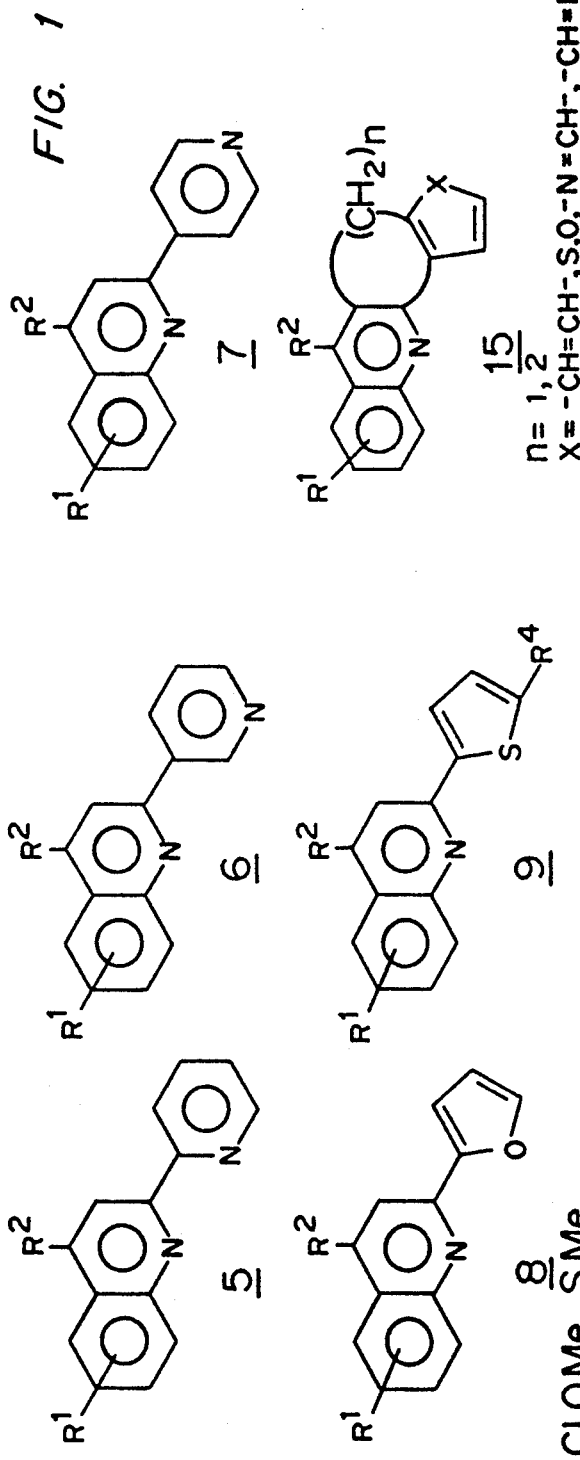

As used herein, the term aliphatic refers to alkyl, aralkyl, alkenyl, alkenylaryl, alkynyl, alkynylaryl, cycloalkyl, nonaromatic cycloalkenyl, and dienyl groups. The term aromatic refers to conjugated cyclic structures with $4n+2$ electrons in the pi shell. The term heteroaromatic refers to any aromatic compounds that include a heteroatom in the ring. The term aprotic refers to aliphatic, aromatic, and heteroaromatic groups that do not contain active hydrogens, including alkyl, alkoxy, alkylthio, alkenyl, halogen, and dialkylamino groups. The term quinoline as referred to here includes fused quinolines including acridines.

In one embodiment, the present invention is a convenient two step process for the preparation of 4-[(alkyl and dialkyl)amino]quinolines of the formulas:

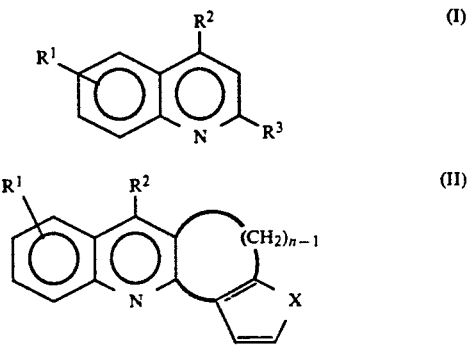

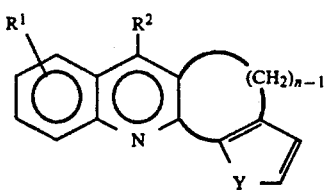

(III)

wherein: $R^1$ is H, 2-chloro, 3-chloro, 4-chloro, 5-chloro, 3-methoxy, 4-methoxy, 5-methoxy, or 4-methylthio (numbering scheme based on parent aniline, wherein $NH_2$ is number 1 in the ring); $R^2$ is an alkylamino or dialkylamino group optionally substituted with aprotic substituents; $R^3$ is an alkenyl, aromatic, or heteroaromatic group optionally substituted with aprotic groups; n is 2 or 3; and X and Y are S, O, HC=CH, N=CH, or CH=N. For example, $R^2$ can be selected from the group consisting of alkylamino, dialkylamino, N, N-dialkylethylenediamino, N-alkylethylenediamino, 4-alkylpiperazino, piperazino, morpholino, thiomorpholino, 1,2,3,4-tetrahydroquinolin-1-yl, indolin-1-yl, 1,2,3,4-tetrahydroisoquinolin-2-yl, and piperidino.

In the first step of the process, illustrated in Schemes I, X, and XII, 2-(trifluoromethyl)aniline or its derivative is condensed with $CH_3C(O)R_3$, wherein $R_3$ is an alkenyl, aromatic, or heteroaromatic group (optionally substituted with aprotic groups), or cyclic ketones 13 or 16, to form intermediate ketimines 12, 14, or 17, respectively. Examples of ketones that can be used in this reaction scheme are described in Tables 1, 12, and 14. Examples of ketimines that can be prepared by this method are listed in Table 2, 12, and 14.

The compound 2-(trifluoromethyl)aniline (also referred to as 2-(trifluoromethyl)benzenamine, as well as 4-chloro-2-(trifluoromethyl)aniline, are commercially available from Aldrich Chemical Company. Methods for the preparation of 3-chloro-2-(trifluoromethyl)aniline, 5-chloro-2-(trifluoromethyl)aniline, and 2-chloro-6-(trifluoromethyl)aniline are known. See Wakselman, et al., European Patent No. 206951; U.S. Pat. No. 4,008,278 to Boudakin et al. 3-Methoxy-2-trifluoromethylaniline and 5-methoxy-2-(trifluoromethyl)aniline can be prepared according to the synthesis described by Wakselman, et al., *J. Chem. Soc., Chem. Commun.* 1701 (1987). 4-Methoxy-2-(trifluoromethyl)aniline can be prepared as described in DE 2788073 to Wolfrum, et al.. The preparation of 4-methythio-2-trifluoromethylaniline is described in DE 2815340 to Ruffing et al., and DE 2551027 to Fridinger, et al.

Noncyclic ketones 11l–11l (See Table 1) are commercially available from Aldrich Chemical Company. The other ketonis listed in Table 1 can be prepared according to the following literature methods: 11m, Ohta, et al., *Heterocycles*, 23(7), 1759 (1985); 11n–11s, Sakamoto, et al., *Synthesis.* 245 (1984); 11t, McNamara, et al., *Tetrahedron*, 40(22), 4685 (1984); 11u, Leardini, et al., *J. Chem. Soc., Chem. Commun.* 1390 (1985); 11v, Miura, et a)., *J. Chem., Soc.* PT1, 1021 (1987).

Cyclic ketones 13 and 16 are also commercially available (6,7-dihydrobenzo[b]thiophen-4(5H)-one, tetralone, and 1-indanone) or can be prepared according to published literature methods. See for example, Coujat, et al., *Tetrahedron Letters* 2885 (1975) (5,6-dihydrobenzo[b]thiophen-7(4H)-one); Thummel, et al., *J. Ore. Chem.* 49, 2208 (1984) (6,7-dihydro-8(5H)-quinolinone); Epsztajn, et al., *J. Chem. Soc.,* PT1, 213 (1985) (7,8-dihydro-5(6H)-quinolinone and 7,8-dihydro-5(6H)isoquinolinone); and Walsh, et al., *Tetrahedron Letters* 27(10), 1127 (1986) (5,6-dihydro-7(4H)-benzo[b-]furanone and 6,7-dihydro-4(5H)-benzo[b]furanone).

In the second step, as illustrated in Schemes II through IX, XI, and XIII, the intermediate ketimines 12, 14, and 17, are reacted with a lithium alkylamide or a lithium dialkylamide to form a 2-substituted-4-(alkylamino or dialkylamino)-6-(substituted)-quinoline, a 5,6-dihydrobenzo[c]acridine derivative, or a H-indenoquinoline. Examples of alkylamides and dialkylamides suitable for reaction with the ketimine are set out in Tables 3–10, 13 and 15 (defined in the Tables as $R_2$). In general, any primary or secondary alkylamine that is capable of forming a lithium salt that reacts with the intermediate ketimine is suitable for this process. The alkylamino and dialkylamino groups can be linear, branched, or cyclic and can optionally include heteroatoms (O, N, and S) in the alkyl chain. The alkylamino and dialkylamino groups can also contain aprotic substituents bonded to the alkyl portions of the molecules, including alkenyl and dialkylamino groups. Further, the dialkyl groups can be linked together covalently to form a cyclic structure such as that found in piperidine, morpholine, and thiomorpholine. In addition to being covalently linked, the dialkyl groups can be part of a tetrahydroheteroaromatic system, such as 1,2,3,4-tetrahydroquinoline, and 1,2,3,4-tetrahydroisoquinoline. Alternatively, the cyclic dialkyl structure can have a fused aromatic or heterocyclic ring attached as in indoline.

This method is suitable for the preparation of quinolines substituted at position 2 ($R_3$) with dialkylvinyl groups, such as compound 2 (see FIG. 1), with aryl groups, such as compounds 3 and 4, and with heteroaryl groups, such as 5–9. The heteroaryl group can be either unsubstituted, as in compounds 4–8 or substituted, as in compound 9. The $R_3$ substituents can be optionally substituted with aprotic groups. Examples of suitable $R_3$ groups are listed in Table 1, and include 2,2-dialkylvinyl, biphenyl-4-yl, 2-naphthyl, 2-pyridinyl, 3-pyridinyl, 4-pyridinyl, 2-furanyl, 2-thienyl, 5-methyl-2-thienyl, 2-thiazolyl, 3-thienyl, 2-benzo[b]furanyl, 2-benzothiazoly, 2-quinolinyl, 1-isoquinolinyl, 4-isoquinolinyl, 3-isoquinolinyl, 3-quinolinyl, 4-quinolinyl, 3-furanyl, 2-benzo[b]thienyl, and 3-benzo[b]thienyl groups. The IUPAC nomenclature, chemical formulas and melting points for quinoline derivatives 2 through 9, or their hydrobromide salts, are provided in Table 11.

The method is also suitable for the preparation of fused quinolines (also referred to as dihydroacridines and H-indenoquinolines) 15 and 18. The dihydroacridine is further derivatized With a fused benzo ring (15a, 15b, 5c, and 15d), thieno ring (15e, 18a), pyridine ring (15g, 5h, 18c, and used), or furanyl ring (15f, 18b).

Scheme I

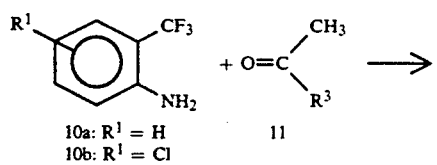

10a: $R^1$ = H
10b: $R^1$ = Cl

11

-continued
Scheme I

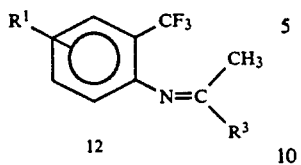

TABLE 1
Starting Ketones 11

| 11 | $R^3$ |
|---|---|
| a | 2-methyl-1-propenyl |
| b | biphenyl-4-yl |
| c | 2-naphthyl |
| d | 2-pyridinyl |
| e | 3-pyridinyl |
| f | 4-pyridinyl |
| g | 2-furanyl |
| h | 2-thienyl |
| i | 5-methyl-2-thienyl |
| j | 2-thiazolyl |
| k | 3-thienyl |
| l | 2-benzofuranyl |
| m | 2-benzothiazolyl |
| n | 2-quinolinyl |
| o | 1-isoquinolinyl |
| p | 4-isoquinolinyl |
| q | 3-isoquinolinyl |
| r | 3-quinolinyl |
| s | 4-quinolinyl |
| t | 3-furanyl |
| u | benzo[b]theien-2-yl |
| v | benzo[b]thein-3-yl |

TABLE 2
Ketimines 12

| 12 | $R^1$ | $R^3$ | Yield (%) | mp (°C.) |
|---|---|---|---|---|
| a | H | 2-methyl-1-propenyl | 60 | oil |
| b | Cl | 2-methyl-1-propenyl | 68 | oil |
| c | H | biphenyl-4-yl | 83 | 137-138 |
| d | Cl | biphenyl-4-yl | 81 | 160-163 |
| e | H | 2-naphthyl | 71 | 87-89 |
| f | Cl | 2-naphthyl | | |
| g | H | 2-pyridinyl | 80 | oil |
| h | Cl | 2-pyridinyl | 82 | oil |
| i | H | 3-pyridinyl | 85 | oil |
| j | Cl | 3-pyridinyl | 84 | 82-84 |
| k | H | 4-pyridinyl | 84 | 72-74 |
| l | Cl | 4-pyridinyl | 80 | oil |
| m | H | 2-furanyl | 80 | 25-27 |
| n | Cl | 2-furanyl | 74 | oil |
| o | H | 2-thienyl | 82 | 67-69 |
| p | Cl | 2-thienyl | 91 | oil |
| q | H | 5-methyl-2-thienyl | 88 | oil |
| r | Cl | 5-methyl-2-thienyl | 80 | 81-83 |

Scheme II

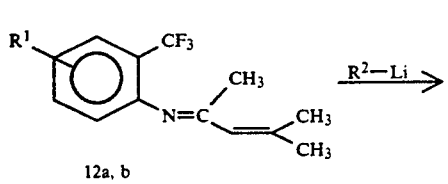

-continued
Scheme II

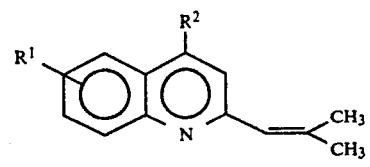

TABLE 3
Quinolines 2

| 2 | $R^1$ | $R^2$ | Formula | Yield (%) |
|---|---|---|---|---|
| a | H | —NHCH$_2$CH$_2$N(CH$_3$)$_2$ | C$_{17}$H$_{23}$N$_3$ | 73 |
| b | Cl | —NHCH$_2$CH$_2$N(CH$_3$)$_2$ | C$_{17}$H$_{22}$ClN$_3$ | 79 |

Scheme III

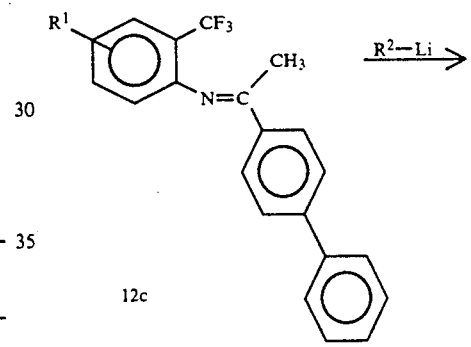

TABLE 4
Quinolines 3

| 3 | $R^1$ | $R^2$ | Formula | Yield (%) |
|---|---|---|---|---|
| a | H | —NHCH$_2$CH$_2$N(CH$_3$)$_2$ | C$_{25}$H$_{25}$N$_3$ | 89 |
| b | H | —N⟨piperazinyl⟩NCH$_3$ | C$_{26}$H$_{25}$N$_3$ | 91 |

Scheme IV

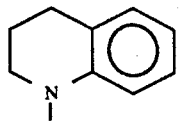

TABLE 5

| 4 | R¹ | R² | Formula | Yield (%) |
|---|----|----|---------|-----------|
| a | H | —NHCH₂CH₂N(CH₃)₂ | $C_{23}H_{23}N_3$ | 95 |

Scheme V

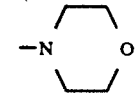

TABLE 6

| 5 | R¹ | R² | Formula | Yield (%) |
|---|----|----|---------|-----------|
| a | H | —NHCH₂CH₂N(CH₃)₂ | $C_{18}H_{20}N_4$ | 82 |
| b | H | CH₃CH₂NCH₂CH₂N(CH₃)₂ | $C_{20}H_{24}N_4$ | 72 |
| c | H | —N(CH₂CH₃)₂ | $C_{18}H_{19}N_3$ | 48 |
| d | H | —N⌒N-NCH₃ | $C_{19}H_{20}N_4$ | 74 |

TABLE 6-continued

| 5 | R¹ | R² | Formula | Yield (%) |
|---|----|----|---------|-----------|
| e | H | (1,2,3,4-tetrahydroquinolin-1-yl) | $C_{23}H_{19}N_3$ | 62 |
| f | H | morpholino | $C_{18}H_{17}N_3O$ | 15 |
| g | H | thiomorpholino | $C_{18}H_{17}N_3S$ | 15 |
| h | H | indolin-1-yl | $C_{22}H_{17}N_3$ | 63 |
| i | Cl | 4-methylpiperazin-1-yl | $C_{19}H_{20}N_4$ | 32 |

Scheme VI

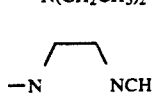

TABLE 7

| 6 | R¹ | R² | Formula | Yield (%) |
|---|----|----|---------|-----------|
| a | H | —NHCH₂CH₂N(CH₃)₂ | $C_{18}H_{20}N_4$ | 85 |
| b | H | CH₃CH₂NCH₂CH₂N(CH₃)₂ | $C_{20}H_{24}N_4$ | 74 |
| c | H | —N(CH₂CH₃)₂ | $C_{18}H_{19}N_3$ | 71 |
| d | H | —N⌒N-NCH₃ | $C_{19}H_{20}N_4$ | 74 |

TABLE 7-continued

Quinolines 6

| 6 | R¹ | R² | Formula | Yield (%) |
|---|----|----|---------|-----------|
| e | H | N-methyl-1,2,3,4-tetrahydroquinolinyl | $C_{23}H_{19}N_3$ | 54 |
| f | H | N-methyl-1,2,3,4-tetrahydroisoquinolinyl | $C_{23}H_{19}N_3$ | 51 |
| g | H | N-methylindolinyl | $C_{22}H_{17}N_3$ | 82 |
| h | H | morpholinyl (−N⌒O) | $C_{18}H_{17}N_3O$ | 35 |
| i | H | thiomorpholinyl (−N⌒S) | $C_{18}N_{17}N_3S$ | 65 |
| j | H | 2-methylpiperidinyl | $C_{20}H_{21}N_3$ | 45 |
| k | H | 3-methylpiperidinyl | $C_{20}H_{21}N_3$ | 60 |
| l | H | 4-methylpiperidinyl | $C_{20}H_{21}N_3$ | 70 |

Scheme VII

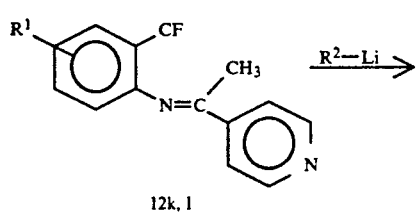

12k, l

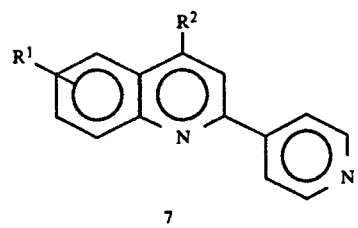

7

TABLE 8

Quinolines 7

| a | R¹ | R² | Formula | Yield (%) |
|---|----|----|---------|-----------|
| a | H | −NHCH₂CH₂N(CH₃)₂ | $C_{18}H_{20}N_4$ | 82 |
| b | H | CH₃CH₂NCH₂CH₂N(CH₃)₂ | $C_{20}H_{24}N_4$ | 88 |
| c | H | −N⌒NCH₃ (N-methylpiperazinyl) | $C_{19}H_{20}N_4$ | 94 |
| d | Cl | −NHCH₂CH₂N(CH₃)₂ | $C_{18}H_{19}ClN_4$ | 36 |

Scheme VIII

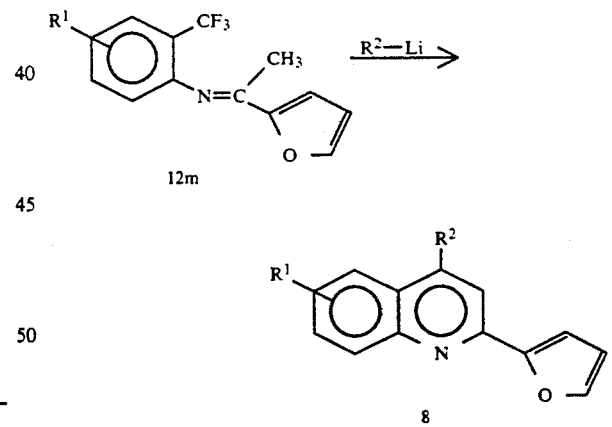

12m

8

TABLE 9

Quinolines 8

| 8 | R¹ | R² | Formula | Yield (%) |
|---|----|----|---------|-----------|
| a | H | −NHCH₂CH₂N(CH₃)₂ | $C_{17}H_{19}N_3O$ | 66 |
| b | H | −N[CH(CH₃)₂]₂ | $C_{19}H_{22}N_2O$ | 78 |
| c | H | −N⌒NCH₃ | $C_{18}H_{19}N_3O$ | 21 |

Scheme IX

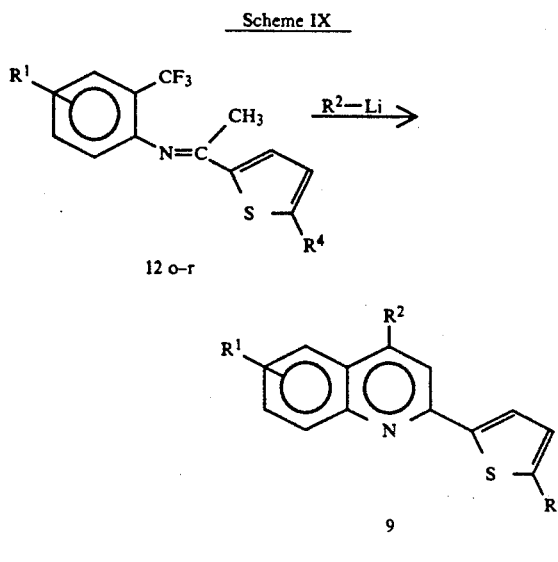

12 o-r

TABLE 10

| 9 | R¹ | R² | R⁴ | Formula | Yield (%) |
|---|----|----|----|---------|-----------|
| a | H | —NHCH$_2$CH$_2$N(CH$_3$)$_2$ | H | C$_{17}$H$_{19}$N$_3$S | 95 |
| b | H | —NHC(CH$_3$)$_3$ | H | C$_{17}$H$_{18}$N$_2$S | 67 |
| c | H | CH$_3$CH$_2$NCH$_2$CH$_2$N(CH$_3$)$_2$ | H | C$_{19}$H$_{23}$N$_3$S | 95 |
| d | H | —N(piperazinyl)NCH$_3$ | H | C$_{18}$H$_{19}$N$_3$S | 91 |
| e | Cl | —NHCH$_2$CH$_2$N(CH$_3$)$_2$ | H | C$_{17}$H$_{18}$ClN$_3$S | 74 |
| f | Cl | —N(piperazinyl)NCH$_3$ | H | C$_{18}$H$_{18}$ClN$_3$S | 84 |
| g | H | —NHCH$_2$CH$_2$N(CH$_3$)$_2$ | CH$_3$ | C$_{18}$H$_{21}$N$_3$S | 82 |
| h | Cl | —NHCH$_2$CH$_2$N(CH$_3$)$_2$ | CH$_3$ | C$_{18}$H$_{20}$ClN$_3$S | 48 |

TABLE 11

Names, formulas, and melting points for quinolines 2-9 or their hydrobromide salts (obtained from non-crystalline quinolines 2-9).

| No | Name | Formula | Mp (°C.) |
|----|------|---------|----------|
| 2a | N-[2-(diemthylamino)ethyl]-2-(2-methyl-1-propenyl)-4-quinolinamine dihydrobromide | C$_{17}$H$_{23}$N$_3$.2HBr.½H$_2$O | 278–280 |
| 2b | 6-chloro-N-[2-(dimethylamino)ethyl]-2-(2-methyl-1-propenyl)-4-quinolinamine | C$_{17}$H$_{22}$ClN$_3$ | 90–92 |
| 3a | 2-(biphenyl-4-yl)-N-[2-(dimethylamino)ethyl]-4-quinolinamine | C$_{25}$H$_{25}$N$_3$.H$_2$O | 129–131 |
| 3b | 2-(biphenyl-4-yl)-4-(4-methylpiperazino)quinoline dihydrobromide | C$_{26}$H$_{25}$N$_3$.2HBr.½H$_2$O | 179–181 |
| 4a | N-[2-(diemthylamino)ethyl]-2-(2-naphthyl)-4-quinolinamine | C$_{23}$H$_{23}$N$_3$.¼H$_2$O | 161–163 |
| 5a | N-[2-(dimethylamino)ethyl]-2-(2-pyridinyl)-4-quinolinamine dihydrobromide | C$_{18}$H$_{20}$N$_4$.2HBr.3/2H$_2$O | 279–282 |
| 5b | N-[2-(diemthylamino)ethyl]-N-ethyl-2-(2-pyridinyl)-4-quinolinamine dihydrobromide | C$_{20}$H$_{24}$N$_4$.2HBr.2H$_2$O | 228–230 |
| 5c | N,N-diethyl-2-(2-pyridinyl)-4-quinolinamine hydrobromide | C$_{18}$H$_{19}$N$_3$.HBr | 210–212 |
| 5d | 4-(4-methylpiperazino)-2-(2-pyridinyl)quinoline dihydrobromide | C$_{19}$H$_{20}$N$_4$.2HBr.H$_2$O | 316–320 |
| 5e | 2-(2-pyridinyl)-4-(1,2,3,4-tetrahydroquinolin-1-yl)-quinoline | C$_{23}$H$_{19}$N$_3$ | 161–162 |
| 5f | 4-morpholino-2-(2-pyridinyl)quinoline | C$_{18}$H$_{17}$N$_3$O | 116–117 |
| 5g | 2-(2-pyridinyl)-4-thiomorpholinoquinoline | C$_{18}$H$_{17}$N$_3$S | 142–143 |
| 5h | 4-indolino-2-(2-pyridinyl)quinoline | C$_{22}$H$_{17}$N$_3$ | 139–140 |
| 5i | 6-chloro-4-(4-methylpiperazino)-2-(2-pyridinyl)quinoline | C$_{19}$H$_{20}$N$_4$ | 162–164 |
| 6a | N-[2-(dimethylamino)ethyl]-2-(3-pyridinyl)-4-quinolinamine trihydrobromide | C$_{18}$H$_{20}$N$_4$.3HBr | 281–283 |
| 6b | N-[2-(dimethylamino)ethyl]-N-ethyl-2-(3-pyridinyl)-4-quinolinamine trihydrobromide | C$_{20}$H$_{24}$N$_4$.3HBr.3H$_2$O | 131–133 |
| 6c | N,N-diethyl-2-(3-pyridinyl)-4-quinolinamine hydrobromide | C$_{18}$H$_{19}$N$_3$.HBr | 230–232 |
| 6d | 4-(4-methylpiperazino)-2-(3-pyridinyl)quinoline | C$_{19}$H$_{20}$N$_4$ | 127–128 |
| 6e | 2-(3-pyridinyl)-4-(1,2,3,4-tetrahydroquinolin-1-yl)-quinoline | C$_{23}$H$_{19}$N$_3$ | 163–164 |
| 6f | 2-(3-pyridinyl)-4-(1,2,3,4-tetrahydroisoquinolin-2-yl)-quinoline | C$_{23}$H$_{19}$N$_3$ | 127–128 |
| 6g | 4-(indolino)-2-(3-pyridinyl)-quinoline | C$_{22}$H$_{17}$N$_3$ | 148–150 |
| 6h | 4-morpholino-2-(3-pyridinyl)quinoline | C$_{18}$H$_{17}$N$_3$O | 131–133 |
| 6i | 2-(3-pyridinyl)-4-thiomorpholinoquinoline | C$_{18}$H$_{17}$N$_3$S | 126–127 |

TABLE 11-continued

Names, formulas, and melting points for quinolines 2–9 or their hydrobromide salts (obtained from non-crystalline quinolines 2–9).

| No | Name | Formula | Mp (°C.) |
|---|---|---|---|
| 6j | 4-(2-methylpiperidino)-2-(3-pyridinyl)quinoline hydrobromide | $C_{20}H_{21}N_3 \cdot HBr \cdot \frac{1}{2}H_2O$ | 235–238 |
| 6k | 4-(3-methylpiperidino)-2-(3-pyridinyl)quinoline hydrobromide | $C_{20}H_{21}N_3 \cdot HBr \cdot \frac{1}{2}H_2O$ | 218–222 |
| 6l | 4-(4-methylpiperidino)-2-(3-pyridinyl)quinoline hydrobromide | $C_{20}H_{21}N_3 \cdot HBr \cdot \frac{1}{2}H_2O$ | 244–246 |
| 7a | N-[2-(dimethylamino)ethyl]-2-(4-pyridinyl)-4-quinolinamine | $C_{18}H_{20}N_4$ | 110–112 |
| 7b | N-[2-(dimethylamino)ethyl]-N-ethyl-2-(4-pyridinyl)-4-quinolinamine trihydrobromide | $C_{20}H_{24}N_4 \cdot 3HBr \cdot H_2O$ | 248–250 |
| 7c | 4-(4-methylpiperazino)-2-(4-pyridinyl)quinoline dihydrobromide | $C_{19}H_{20}N_4 \cdot 2HBr \cdot 3/2H_2O$ | 226–229 |
| 7d | 6-chloro-N-[2-(dimethylamino)ethyl]-2-(4-pyridinyl)-4-quinolinamine | $C_{18}H_{19}ClN_4$ | 120–121 |
| 8a | N-[2-(dimethylamino)ethyl]-2-(2-furanyl)-4-quinolinamine | $C_{17}H_{19}N_3O$ | 93–95 |
| 8b | N,N-diisopropyl-2-(2-furanyl)-4-quinolinamine hydrobromide | $C_{19}H_{22}N_2O \cdot HBr$ | 195–196 |
| 8c | 2-(2-furanyl)-4-(4-methylpiperazino)quinoline dihydrobromide | $C_{18}H_{19}N_3O \cdot 2HBr \cdot H_2O$ | 335–340 |
| 9a | N-[2-(dimethylamino)ethyl]-2-(2-thienyl)-4-quinolinamine | $C_{17}H_{19}N_3S$ | 109–110 |
| 9b | N-(tert-butyl)-2-(2-)thienyl-4-quinolinamine | $C_{17}H_{18}N_2S$ | 96–98 |
| 9c | N-[2-(dimethylamino)ethyl]-N-ethyl-2-(2-thienyl)-4-quinolinamine dihydrobromide | $C_{19}H_{23}N_3S \cdot 2HBr \cdot 2H_2O$ | 263–264 |
| 9d | 4-(4-methylpiperazino)-2-(2-thienyl)quinoline dihydrobromide | $C_{18}H_{19}N_3 \cdot 2HBr \cdot 2H_2O$ | 330–334 |
| 9e | 6-chloro-N-[2-(dimethylamino)ethyl]-2-(2-thienyl)-4-quinolinamine | $C_{17}H_{18}ClN_3S$ | 150–151 |
| 9f | 6-chloro-4-(4-methylpiperazino)-2-(2-thienyl)quinoline | $C_{18}H_{18}ClN_3S$ | 120–122 |
| 9g | N-[2-(dimethylamino)ethyl]-2-(5-methyl-2-thienyl)-4-quinolinamine | $C_{18}H_{21}N_3S$ | 103–105 |
| 9h | 6-chloro-N-[2-(dimethylamino)ethyl]-2-(5-methyl-2-thienyl)-4-quinolinamine | $C_{18}H_{20}ClN_3S$ | 119–120 |

Scheme X

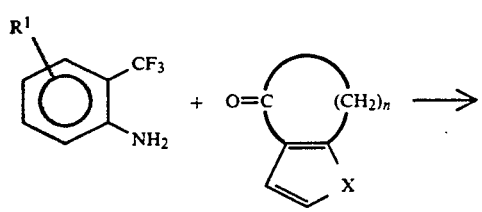

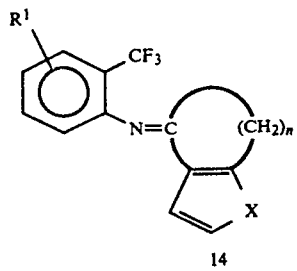

$n = 2, 3$
$X = -CH=CH-, S, O, -N=CH-, -CH=N-$

TABLE 12

| 14 | Ketimines 14 | | |
|---|---|---|---|
| | $R^1$ | n | X |
| a | H | 3 | —CH=CH— |
| b | H | 2 | —CH=CH— |
| c | Cl | 3 | —CH=CH— |
| d | H | 3 | S |
| e | Cl | 3 | S |
| f | H | 3 | O |
| g | H | 3 | —N=CH— |
| h | H | 3 | —CH=N— |

Scheme XI

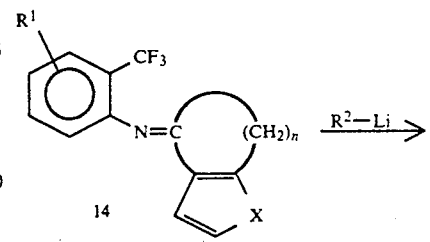

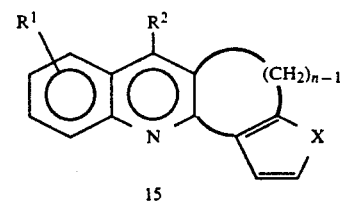

$n = 2, 3$
$X = -CH=CH-, S, O, -N=CH-, -CH=N-$

TABLE 13

| 15 | Fused quinolines 15 | | | |
|---|---|---|---|---|
| | $R^1$ | $R^2$ | n | X |
| a | H | $-NHCH_2CH_2N(CH_3)_2$ | 3 | —CH=CH— |
| b | H | | 3 | —CH=CH— |
| c | Cl | $-NHCH_2CH_2N(CH_3)_2$ | 3 | —CH=CH— |
| d | H | $-NHCH_2CH_2N(CH_3)_2$ | 2 | —CH=CH— |

TABLE 13-continued

| 15 | R¹ | Fused quinolines 15 R² | n | X |
|---|---|---|---|---|
| e | H | 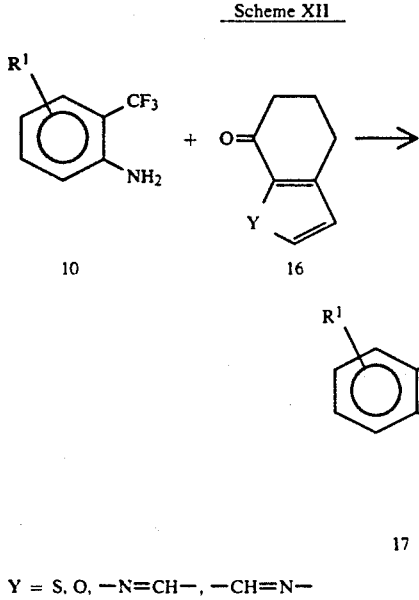 (−N⏜NCH₃) | 3 | S |
| f | H | −NHCH₂CH₂N(CH₃)₂ | 3 | O |
| g | H | −NHCH₂CH₂N(CH₃)₂ | 3 | −N=CH− |
| h | H | −NHCH₂CH₂N(CH₃)₂ | 3 | −CH=N− |

Scheme XII

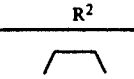

Y = S, O, −N=CH−, −CH=N−

TABLE 14

| 17 | Ketimines 17 R¹ | Y |
|---|---|---|
| a | H | S |
| b | H | O |
| c | H | −N=CH− |

Scheme XIII

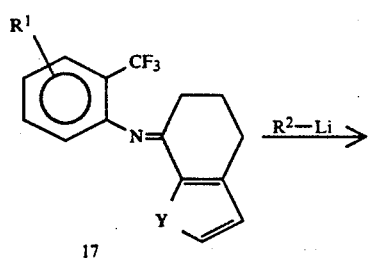

R²−Li →

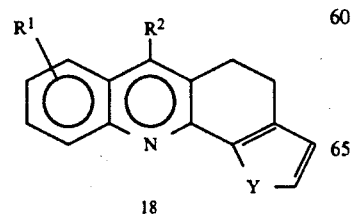

-continued
Scheme XIII

Y=S, O, −N=CH−, −CH=N−

TABLE 15

| 18 | R¹ | Fused quinolines 18 R² | Y |
|---|---|---|---|
| a | H | −NHCH₂CH₂N(CH₃)₂ | S |
| b | H |  (−N⏜NCH₃) | O |
| c | H | −NHCH₂CH₂N(CH₃)₂ | −N=CH− |

TABLE 16

Medium effective concentrations ($EC_{50}$) of quinolines against HIV-1 as determined in human peripheral blood mononuclear (PBM) cells infected with HIV-1 (strain LAV).

| Quinoline | $EC_{50}$ (μM) |
|---|---|
| 5a | 1.1 |
| 5b | 13.2 |
| 5d | 5.5 |
| 6a | 1.5 |
| 6b | 24.2 |
| 6d | 1.0 |
| 7c | 68.2 |
| 8a | 0.9 |
| 8c | 1.0 |
| 8d | 15.8 |
| 9a | 1.0 |
| 9c | 32.4 |

The new 4-[(alkyl and dialkyl)amino]quinolines described herein are useful as agents that bind to DNA, and are capable of amplifying the effect of drugs that bind to DNA, for example, the known anticancer agents bleomycin and phleomycin. These compounds also exhibit selective in vitro inhibition of retroviruses, including HIV-1, the etiological agent of acquired immunodeficiency syndrome (AIDS).

In a third embodiment, the present invention provides new ketimines of the formulas:

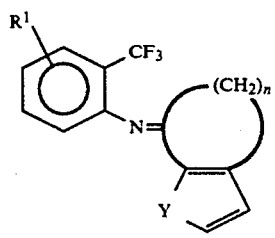

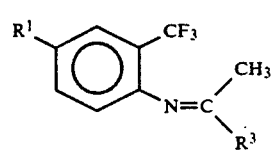

-continued

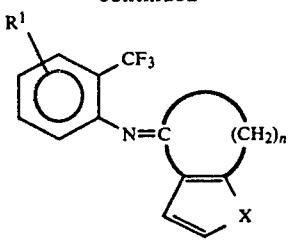

wherein: R¹ is H, 2-chloro, 3-chloro, 4-chloro, 5-chloro, 3-methoxy, 4-methoxy, 5-methoxy, or 4-methylthio; R³ is an alkenyl, aromatic, or heteroaromatic group optionally substituted with aprotic groups; n is 2 or 3; and X and Y are HC=CH, N=CH, CH=N, O, or S.

These compounds are useful as intermediates in the preparation of the active 4-[(alkyl and dialkyl)amino]-quinolines described herein.

This invention is further illustrated by the following nonlimiting examples describing the method of synthesis and use of these compounds.

I. Method of Preparation of 4-[(Alkyl and Dialkyl)amino]quinolines

The starting materials for the 4-[(alkyl and dialkyl)amino]quinolines are 2-(trifluoromethyl)anilines 10 and ketones 11, 13 and 16. (see Scheme I and Table 1). In the following discussion, for ease of illustration, the method is described with reference to the reaction of 2-(trifluoromethyl)aniline or 4-chloro-2-(trifluoromethyl)aniline with the noncyclic ketone followed by cyclization of the resulting ketimine to form the corresponding quinoline derivative. However, it should be understood that the present invention is not limited to this examples but includes all of the described combinations of starting materials and products.

In the first step, a mixture of 10 and 11 and a catalytic amount of an acid catalyst, such as p-TsOH (p-toluenesulfonic acid) in an aromatic hydrocarbon solvent such as benzene or toluene is heated under reflux with azeotropic removal of water. This condensation reaction is monitored by measuring the volume of water formed during the condensation. It is typically completed within three to fifteen hours. The time of reaction will vary depending on the reagents and solvent used. The crude ketimine is isolated by removal of the solvent by evaporation and is then purified by distillation under reduced pressure. The conditions of distillation will vary based on the structure of the ketimine. In general, the distillation is carried out at a temperature between 100°-150° C. and at a pressure of between 0.1-0.5 mm Hg. The ketimines 12 (Scheme I and Table 2) thus obtained are sufficiently pure to be used in the second synthetic step of the process.

A solution of a primary or secondary alkylamine in an ether solvent, such as diethyl ether or tetrahydrofuran, under anhydrous conditions, is treated with one molar equivalent of a solution of commercial lithium reagent, such as methyllithium or butyllithium. The solution or suspension of the lithium amide is then treated with a solution of ketimine 12, and the reaction mixture is stirred for 0.5-2 hours. The preferred molar ratio of the lithium amide to the ketimine is 4:1. The preferred reaction temperature is between −10° and +10° C. for lithium reagents derived from primary amines and between −20° and −10° C. for lithium reagents derived from secondary amines. The progress of the reaction is conveniently monitored by thin layer chromatography on silica gel. When the reaction is completed, it is quenched with water. The crude quinoline is purified on a short chromatography column packed with silica gel with a mixture of hexanes/triethylamine/ethanol (7:2:1) as an eluent. The final purification of solid quinolines includes crystallization from a hydrocarbon solvent such as hexanes. Non-crystalline quinolines are conveniently purified by treatment with an acid, preferably hydrobromic acid, and crystallization of the resultant salt from an alcohol, such as ethanol, or a mixture of ethanol with hexanes.

The structural formulas of quinoline derivatives obtained by this method are given in Schemes II-IX, XI, and XIII and the corresponding Tables 3-10, 13, and 15. As can be seen from Tables 3-10, the yields of isolated quinolines 2-9 are good to excellent with only a few exceptions. The IUPAC nomenclature for compounds 2-9 are given in Table 11.

The following non-limiting examples provide detailed procedures for the synthesis of ketimines such as 12q and substituted quinolines such as 9g.

N-[1-(5-Methyl-2-thienyl)ethylidene]-2-(trifluoromethyl)aniline (12q)

A solution of 2-(trifluoromethyl)aniline (4.0 q, 25 mmol), 2-acetyl-5-methylthiophene (4.4 g, 31 mmol), and p-toluenesulfonic acid (50 mg) in toluene (30 mL) was heated under reflux with azeotropic removal of water for 10 hours. Then the mixture was concentrated on a rotary evaporator, and the oily residue was distilled under reduced pressure to give 6.2 g (88%) of ketimine 12q as an oil (bp 128°-130° C./0.3 mm Hg).

Other ketimines 12 were prepared in a similar manner. Crystalline compounds 12 were additionally crystallized from hexanes.

N-[2-(dimethylamino)ethyl]-2-(5-methYl-2-thienyl)-4-quinolinamine (9g)

A solution of N,N-dimethylethylenediamine (0.66 ml, 6.0 mmol) in ether (15 mL) was treated with a commercial solution of n-butyllithium (6.0 mmol) in hexanes at −10° C., and the resultant mixture was stirred at −10° C. for 20 minutes before treatment with a solution of ketimine 12q (0.42 g, 1.5 mmol) in ether (5 mL). The mixture was stirred at −10° C. for an additional 45 minutes, and then quenched with water (0.5 mL). The organic layer was concentrated on a rotary evaporator to give a crystalline residue. Removal of colored polymeric materials on a short silica gel column by eluting quinoline 9g with hexanes/Et₃N/EtOH (7:2:1) was followed by crystallization of the purified 9g from hexanes; yield 82%, mp 103°-105° C.

Other quinolines 2-9 were prepared in a similar manner using the appropriate ketimines 12 and lithium amide reagents.

Hydrobromide salts of 2-9

Non-crystalline quinolines 2-9 were transformed into crystalline hydrobromide salts. Thus, a solution of a quinoline derivative in ethanol was treated with a solution of hydrobromic acid in aqueous ethanol, and the resultant mixture was concentrated to precipitate the hydrobromide salt. The salt was crystallized from ethanol or the mixture of ethanol with hexanes. The composition of the salt was determined by elemental analysis.

II. Biological Activities of 4-[(Alkyl and Dialkyl)amino]quinolines

EXAMPLE 1

Intercalation of DNA and Amplication of the activity of Anticancer Agents

One method of enhancing the activity of currently available anticancer drugs is to identify compounds that alone may or may not have significant anticancer activity but that amplify the action of the drug when administered together. For example, bleomycin and phleomycin metal complexes have anticancer activity because they bind to DNA and disrupt the double helix. The anticancer activity of bleomycin and phleomycin can be enhanced by DNA intercalators and groove binding agents that distort the double helix. See generally: Strekowski, et al., "Molecular Basis for Anticancer Drug Amplification: Interaction of Phleomycin Amplifiers with DNA," *J. Med. Chemistry Vol.* 29, 1311 (1986); Strekowski, et al., "A Non-classical Intercalation model for a Bleomycin Amplifier," *Anti-Cancer Druo Design* Vol. 2, 387 (1988).

The 4-[(alkyl and dialkyl)amino]quinolines of the present invention are capable of inserting into and distorting the DNA helix. The interaction of these compounds with nucleic acids involves two features: (i) electrostatic attraction of the protonated amino group with the anionic backbone of the nucleic acid an (ii) intercalation of the quinoline derivative with the nucleic acid acid base-pairs. This double-interaction mode is important for the enhancement (amplification) of anti-cancer activity of nucleic acid-interacting drugs such as phleomycin and bleomycin. It appears that the presence of an additional amino substituent in the 4-amino side group enhances the interaction of the substituted quinoline with nucleic acids. This additional amino substituent is strongly basic ($pk_a \sim 9$-10) and is, therefore, protonated under physiological conditions.

The ability of a compound to insert into DNA can be measured by increase in DNA viscosity (using viscometric titration with isolated DNA samples), flow dichroism, and is evident from a downfield shift of DNA $^{31}P$ signals, and an upfield shift of hydrogen-bonded base-pair imino protons. In addition, the NMR signals for the aromatic protons of the quinoline are shifted upfield depending on the extent of overlap of the pi clouds of the quinoline and the base pairs in the DNA. Detailed procedures for the measurement of the extent of intercalation of the quinoline derivatives with DNA are provided below. Sonicated calf thymus DNA (Worthington Biochemical) is used in the viscometric titrations ($800\pm100$ base pairs) as well as the NMR experiments ($200\pm50$ base pairs). An unsonicated DNA sample is used in the flow dichroism studies.

A. Viscometric Titration with DNA.

All DNA samples are purified from residual proteins and characterized as previously described (Wilson, et al., *Biopolymers* 24, 1941 1985)). Plasmid pBR322 for the viscometric titrations is obtained from *Eschericia coli* strain K336 grown in Luria-Bertani media with 25 $\mu gl^{-1}$ ampicillin and amplified with $100 mgl^{-1}$ chloramphenicol (Hillen, et al., *Biochemistry* 20, 3748 (1981)). After the usual workup described by Garger, et al., *Biochem. and BioDhvs. Res. Comm.* 117, 835 (1983), the plasmid (concentration of $3 \times 10^{-3}$ M DNA bases) is obtained by high performance liquid chromatography on a $10 \times 25$ mm Nucleogen DEAE 4000-7 column (5 M urea, 20 mM $K_3PO_4$, pH 6.9, linear increasing of concentration of KCl from 0.3 M to 1.5 M over 40 minutes, flow rate 2 ml $min^{-1}$) followed by dialysis in a PIPES 00 buffer at 4° C. Electrophoresis shows greater than 95% of supercoiled form I, greater than 5% of circular form II, and an absence of linear form III. When stored with one drop of chloroform at 4° C., the sample does not significantly change its composition over a period of one month.

Viscometric titrations are conducted at $25°\pm0.01°$ C. in PIPES 00 Buffer as previously described by Jones, et al., in *Nucleic Acids Research* 8, 1613 (1980)). The ethidium-induced unwinding angle of 26 is taken as a reference value for the experiments with a superhelical DNA sample (Wang, *J. Mol. Biol.* 89, 783 (1974)). The unwinding experiments are conducted at a range of DNA concentrations and the maximum viscosity changes are plotted by the Vinograd method (Revet, et al., *Nature New Biology* 229, 10 (1971)).

B. Flow Diohroism

Flow dichroism experiments are carried out in a PIPES buffer at 25° C. at a ratio of 0.10 (compound/base pair) and a DNA base pair concentration of 3.65 mM as described by Banville, et al., *Biopolymers* 25, 1837 (1986)).

C. Nuclear Magnetic Resonance Studies.

Measurements of the effect of the new quinolines on DNA imino protons and $^{31}P$ NMR signals are performed as described by Wilson, et al., *J. Am. Chem. Soc.* 107, 4989 (1985). The changes in chemical shift of the aromatic protons of the new quinolines on addition of DNA are measured as follows. Proton (270-MHz) NMR spectra are obtained on a JEOL GX 270 spectrometer under the following conditions: typically 2000 scans; 2.15-s pulse repetition rate; 0.1-Hz line broadening; 16K data points; TSP reference; 4000-Hz spectral width; 100% $D_2O$/phosphate buffer containing 15 mM $NaH_2PO_4$, 0.1 mM EDTA, 0.1 M NaCl; 5 mM quinoline; temperature 60° C.; 0.8-mL sample volume in a 5-mm NMR tube. The high temperature is used to obtain monomer ligand at NMR concentrations and to obtain fast exchange between free and bound compound. Spectrophotometric measurements indicate that the DNA Tm under these conditions is greater than 75° C. and that the DNA is, thus, in the native state in the NMR experiments.

Bleomycin Amplification

Bleomycin-mediated degradation of DNA results in decreases in the viscosity of DNA solution. The relative viscosity changes in the absence and presence of amplifiers are used as a highly sensitive test for bleomycin amplification, as described by Strekowski et al. in *J. Med. Chem.* Vol 31, 1231 (1988).

In the experiment the molecular ratios of DNA to bleomycin and oxygen to DNA should be high. The concentration of ferrous ion remains practically constant throughout the reaction because a relatively high initial concentration of the ferrous ion and dithiothreitol, an iron reducing agent, are used. Under these conditions the DNA viscosity changes over time can be described by the following biphasic equation (1), $$(n/n_o)_t = 0.30\ (\pm0.07)e^{-k_f t} + 0.71\ (\pm0.09)e^{-K_s t} \quad (1)$$

where $n_o$ is the initial reduced specific viscosity for DNA before the addition of bleomycin, n is the reduced specific viscosity for DNA at the reaction (degradation) time t, $k_f$ is the apparent rate constant for the first (fast)

process, and $k_s$ is the apparent rate constant for the second (slow) process. Both fast and slow processes are enhanced in the presence of bleomycin amplifiers. These effects are concentration dependent, that is the viscosity is decreasing faster with increasing concentrations of the amplifiers. The best bleomycin amplifiers are quinolines at general structures 3,4,6,7, and 9 containing an additional amnio group in the 4-alkylamino or 4-dialkylamino substituent.

DNA-Bleomycin Reactions: Concentrations. PIPES 00 buffer (without EDTA, pH 7.00) and high molecular weight DNA are used in all experiments with bleomycin. Stock solutions (37° C.) are added in the order given below to the PIPES 00 buffer in a viscometer to reach the final volume of 1.5 mL and the following final concentrations: calf thymus DNA, $2.34 \times 10$. M (concentration of nucleotide equivalents); compounds 2-9, 15, $4.3 \times 10^{-5}$ M or $4.3 \times 10^{-4}$ M (ratios of 0.37 or 3.7 of molecules per DNA base pair, respectively); FeSO , $7.4 \times 10^{-6}$ M; dithiothreitol, $18 \times 10^{-4}$ M; bleomycin, $1.1 \times 10^{-6}$ M.

EXAMPLE 2

Inhibition of Replication of HIV virus in vitro

The 4-[(alkyl or dialkyl)amino]quinolines exhibit an inhibitory effect on retroviruses, and in particular, human immunodeficiency virus (HIV).

The median effective concentrations ($EC_{50}$) of selected quinolines against HIV-1 were determined in human blood mononuclear (PBM) cells infected with HIV-1 (strain LAV) as described below. The results are provided in Table 16. As shown in Table 16, the $EC_{50}$ values for the quinolines tested range from 0.9 to 68.2. It appears that the presence of a heteraromatic substituent at position 2 of the quinoline enhances the anti-HIV-1 activity of the 4-[(alkyl and dialkyl)amino]quinoline derivative. The anti-HIV-1 activity appears to be diminished in compounds with large substituents attached to the 4-amino group.

The following procedure was used to determine the $EC_{50}$ values for selected compounds.

A. Three-day-old phytohemagglutinin-stimulated PBM cells ($10^6$ cells/ml) from hepatitis B and HIV-1 seronegative healthy donors were infected with HIV-1 (strain LAV) at a concentration of about 100 times the 50% tissue culture infectious dose (TICD 50) per ml and cultured in the presence and absence of various concentrations of quinolines.

B. Approximately 45 minutes after infection, medium, with the compound to be tested (2 times the final concentration in medium) or without compound, was added to the flasks (5 ml; final volume 10 ml). AZT was used as a positive control.

C. The cells were exposed to HIV (about $2 \times 10^5$ dpm/ml, as determined by reverse transcriptase assay) and then placed in a $CO_2$ incubator. HIV-1 (strain LAV) was obtained from the Center for Disease Control, Atlanta, Ga. The methods used for culturing the PBM cells, harvesting the virus and determining the reverse transcriptase activity were those described by McDougal et al. (*J. Immun. Meth.* 76, 171-183, 1985) and Spira et al. (*J. Clin. Meth.* 25, 97-99, 1987), except that fungizone was not included in the medium (see Schinazi, et al., *Antimicrob. Agents Chemother.* 32, 1784-1787 (1988)). The reverse transcriptase activity in the virus-infected control was about $2 \times 10^5$ dpm per ml.

Blank and uninfected cell control values were about 300 and 1,000 dpm, respectively.

D. On day 6, the cells and media were transferred to a 15 ml tube and centrifuged at about 900 g for 10 minutes. Five ml of supernatant were removed and the virus concentrated by centrifugation at 40,000 rpm for 30 minutes (Beckman 70.1 Ti rotor). The solubilized virus pellet was processed for determination of the levels of reverse transcriptase. Results are expressed in dpm/ml of sampled supernatant.

The median effective ($EC_{50}$) concentrations for derivatized quinolines, were determined by the median effect method (Antimicrob. Agents Chemother. 30: 491-498, 1986). Briefly, in the median effect method, the percent inhibition of virus, as determined from measurements of reverse transcriptase, is plotted versus the micromolar concentration of compound. The $EC_{50}$ is the concentration of compound at which there is a 50% inhibition of viral replication.

EXAMPLE 4

Determination of Toxicity of 4-[(Alkyl and Dialkyl)amino]quinolines in Peripheral Blood Mononuclear Cells Assay.

The toxicity of 6a,6d,8a, and 8c were determined in nitrogen-stimulated PBM cells ($3.8 \times 10^5$ cells/ml) cultured in the presence and absence of compounds under conditions similar to those used for the antiviral assay described above but without virus. The cells were counted after 6 days using a hemacytometer and the trypan blue exclusion method, as described by Schinazi et al., *Antimicrobial Agents and Chemotherapy*, 22(3), 499 (1982).

Results.

The effect of the compounds on the growth of uninfected human PBM cells in culture is used as an indicator of the toxicity of the test compound to the normal viability of cells. The $IC_{50}$ is the concentration of compound which inhibits 50% of normal, uninfected, cell growth. Compounds 6a,6d,8a, and 8c were found to have an $IC_{50}$ of greater than 100 μM. Compound 8a has an $IC_{50}$ of 1.2.

Modifications and variations of the present invention, new 4-[alkyl and dialkyl)amino]quinolines and their method of preparation, will be obvious to those skilled in the art from the foregoing description. Such modifications and variations are intended to come within the scope of the appended claims.

We claim

1. 4-[(alkyl or dialkyl)amino]quinolines of the formulas:

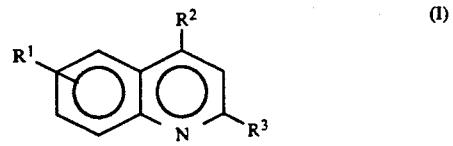

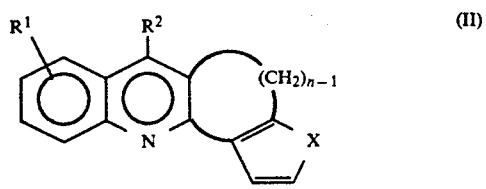

-continued

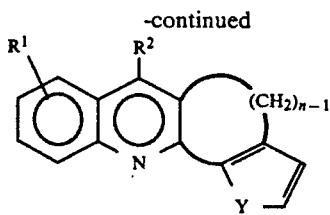

(III)

wherein:
- $R^1$ is H, 2-chloro, 3-chloro, 4-chloro, 5-chloro, 3-methoxy, 4-methoxy, 5-methoxy, or 4-methylthio (numbering scheme based on parent aniline);
- $R^2$ is selected from the group consisting of alkylamino; dialkylamino; N,N-dialkylethylenediamino; N-alkylethylenediamino; 4-alkylpiperazino; piperazino; morpholino; thiomorpholino; 1,2,3,4-tetrahydroisoquinolin-2-yl and piperidino;
- $R^3$ is 2,2-dialkylvinyl, 2-pyridinyl, 3-pyridinyl, 4-pyridinyl, 2-furanyl, 2-thienyl, 2-thiazolyl, 3-thienyl, 2-benzofuranyl, 2-quinolinyl, 1-isoquinolinyl, 4-isoquinolinyl, 3-isoquinolinyl, 3-quinolinyl, 4-quinolinyl, 3-furanyl, 2-benzothienyl, or 3-benzothienyl groups; n is 2 or 3; and X and Y are N=CH, CH=N, O, or S.

2. The 4-[(alkyl or dialkyl)amino]quinolines of claim 1, wherein $R_1$ is 4-chloro.

3. The quinoline of claim 1, wherein $R_3$ is selected from the group consisting of 2,2-dialkylvinyl, 2-pyridinyl, 3-pyridinyl, 4-pyridinyl, 2-furanyl, and 2-thienyl.

4. The quinoline of claim 1, formula III, wherein Y is S.

5. The quinoline of claim 1, formulas II or III, wherein n is 3.

6. The quinoline of claim 1, wherein the $R_2$ group is selected from the group consisting of linear, branched, and cyclic alkyl amino groups.

7. The quinoline of claim 1, wherein the dialkyl amino groups are linked together covalently to form an aliphatic cyclic structure.

8. The quinoline of claim 1, wherein the cyclic structure is selected from the group consisting of piperidine, morpholine, and thiomorpholine.

9. The compounds of claim 1 wherein $R^3$ is 2,2-dialkylvinyl.

* * * * *